United States Patent [19]

Acharya et al.

[11] Patent Number: 5,726,327
[45] Date of Patent: Mar. 10, 1998

[54] PROCESS FOR THE PRODUCTION OF PETROCHEMICALS

[75] Inventors: Divyanshu R. Acharya, Bridgewater, N.J.; Ravi Kumar, Allentown, Pa.; Ramakrishnan Ramachandran, Allendale, N.J.

[73] Assignee: The BOC Group, Inc., New Providence, N.J.

[21] Appl. No.: 721,493

[22] Filed: Sep. 27, 1996

[51] Int. Cl.$^6$ ............................... C07D 307/60
[52] U.S. Cl. .................... 549/258; 549/256; 549/257; 549/259; 549/260
[58] Field of Search ........................ 549/256, 257, 549/258, 259, 260

[56] References Cited

U.S. PATENT DOCUMENTS 4,231,943  11/1980  Parades et al. ................. 549/259

FOREIGN PATENT DOCUMENTS 2544972  4/1977  Germany.

*Primary Examiner*—Bernard Dentz
*Attorney, Agent, or Firm*—Coleman R. Reap; Salvatore P. Pace

[57] ABSTRACT

Petrochemicals are produced by the vapor phase reaction of a hydrocarbon with air in the presence of a suitable catalyst. The petrochemical product is removed from the product gas stream, and unreacted hydrocarbon in part or all of the remaining gas stream is recovered by subjecting the gas stream to a TSA process in which the adsorbed hydrocarbon is desorbed at elevated pressure by purging the adsorbent with hot compressed air, the air being heated by compression. The compressed air-desorbed hydrocarbon mixture is recycled to the reactor.

26 Claims, 1 Drawing Sheet

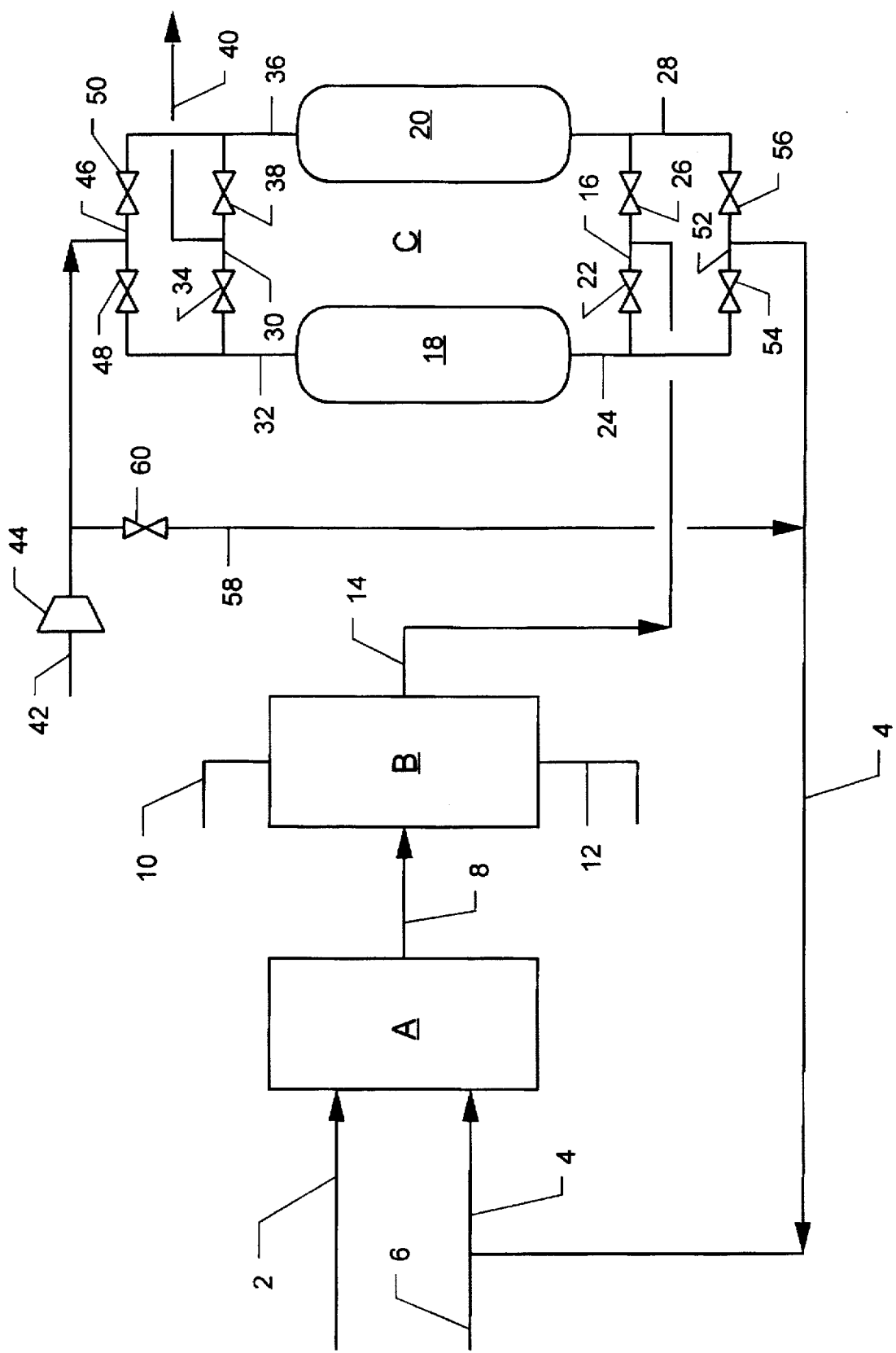

PROCESS FOR THE PRODUCTION OF PETROCHEMICALS

FIELD OF THE INVENTION

The present invention is directed to a process for producing petrochemicals from a hydrocarbon and an oxygen-containing gas in the presence of a suitable catalyst, and more particularly to a hydrocarbon partial oxidation process in which unreacted hydrocarbon separated from other components of a gaseous waste stream is recycled to the partial oxidation reactor.

BACKGROUND OF THE INVENTION

Certain petrochemicals are produced commercially by the partial oxidation of an appropriate hydrocarbon in the vapor phase over a suitable catalyst and in the presence of an oxygen-containing gas. For example, cyclic anhydrides are produced commercially by the vapor phase catalytic partial oxidation of aromatic hydrocarbons, such as o-xylene or benzene, or straight-chain hydrocarbons, such as n-butane, or butene, in the presence of an oxygen-containing gas, over a vanadium-containing catalyst. Similarly, nitriles, alkylene oxides, aldehydes and halogenated hydrocarbons are produced by the partial oxidation of appropriate alkanes and alkenes in the presence of selected catalysts. Air is generally used as the oxygen-containing gas, because of its low cost and ready availability; however, oxygen or oxygen-enriched air can also be used in these processes. The reaction can be carried out in any suitable reactor, such as a fixed bed, a fluidized bed, a moving bed, a trickle bed or a transport bed reactor, and it produces the petrochemical, and generally carbon monoxide (CO), carbon dioxide ($CO_2$), water, and smaller amounts of other partially oxidized by-products. The reaction equipment train generally consists of a reactor, in which the petrochemical product is produced, a scrubber, in which the petrochemical product is scrubbed from the reactor effluent gases by means of water or other solvent for the petrochemical, and means for further treating the scrubbed effluent gases.

Currently, it is common to practice the above-described process on a single pass basis with the conversion of hydrocarbon to the desired petrochemical product being maximized. This results in a low overall efficiency, since the selectivity to petrochemical product is below the maximum. Consequently, the scrubber effluent gas contains considerable amounts of CO and $CO_2$, in addition to unreacted hydrocarbon. These products are usually incinerated, so that the only return realized from them is heat value. In modified processes, a portion of the scrubber effluent gas is recycled, the conversion of the hydrocarbon feedstock is lowered and the selectivity of hydrocarbon conversion to the desired petrochemical product is increased. The remainder of the effluent are purged from the system to prevent the build-up of CO, $CO_2$ and nitrogen (introduced into the system when air is used as the source of oxygen). These improvements result in a reduced "per pass" conversion, but the overall efficiency of the process is increased.

Federal Republic of Germany (FRG) Patent Application Disclosure 25 44 972 discloses a maleic anhydride manufacturing process in which the reactor feed comprises $C_4$ hydrocarbons, air, CO and $CO_2$. In the process of this patent, maleic anhydride is recovered from the reactor effluent gas stream and a portion of the remaining stream is recycled to the reactor. This patent also teaches recovering butane by temperature swing adsorption (TSA) from the non-recycled gas stream and recycling the recovered butane to the reactor. The butane is desorbed from the adsorbent at elevated temperature using fresh air as the purge gas, and the air-butane mixture is recycled to the reactor.

U.S. Pat. No. 4,231,943 discloses the production of maleic anhydride by the reaction of n-butane and air in the presence of a catalyst comprising vanadium and phosphorus oxides. The process of this patent includes the steps of recovering maleic anhydride from the gaseous oxidation reactor effluent, directly recycling a portion of the maleic anhydride-free effluent to the reactor, separating relatively pure n-butane from the remaining gaseous effluent and recycling the relatively pure n-butane to the feed stream.

U.S. Pat. No. 4,987,239 discloses a process for the production of anhydrides by the partial oxidation reaction of a hydrocarbon with an oxygen-containing gas in the presence of a suitable catalyst. In the process of this patent, the gaseous effluent from the maleic anhydride product scrubber is compressed and sent to a selective separator, e.g. a pressure swing adsorption (PSA) unit, wherein a substantial proportion of the unreacted hydrocarbon contained in the effluent is recovered, and the unreacted hydrocarbon and a controlled amount of a gaseous flame suppresser is recycled to the partial oxidation reactor.

It is known to remove moisture from hydrocarbon containing streams and ambient air streams associated with partial oxidation systems by various techniques. For example the air and gas streams can be dried by passing the air and gas stream through desiccants. U.S. patent application Ser. No. 08/494,293, filed Jun. 23, 1995 now U.S. Pat. No. 5,646,304, discloses a recycle partial oxidation process in which a hydrocarbon-containing waste gas from the product scrubber is passed through an adsorber that is operated on a PSA cycle or a concentration swing adsorption (CSA) cycle to recover the hydrocarbon from the waste gas for recycle. The waste gas feed to the hydrocarbon adsorber and air that is used to purge the hydrocarbon from the adsorbent are dried prior to introduction into the hydrocarbon adsorber to prevent moisture saturation of the adsorbent in the hydrocarbon adsorbent.

It is also known to use a hydrophobic adsorbent in a PSA or CSA cycle for hydrocarbon recovery in a recycle partial oxidation process, thereby avoiding the need to dry the hydrocarbon feed and air purge gas streams prior to their introduction into the hydrocarbon recovery adsorber. Such a process is disclosed in U.S. patent application Ser. No. 08/457,003, filed Jun. 1, 1995. The texts of U.S. patent applications Nos. 494,293 and 457,003 are incorporated herein by reference.

In the processes described in U.S. patent applications Nos. 494,293 and 457,003, the hydrocarbon partial oxidation reactor is operated at superatmospheric pressure, the pressure being provided by compressing the air feed stream to the reactor in a main air compressor. However the hydrocarbon separation system is located upstream of the main air compressor; accordingly, if all of the air used in the partial oxidation reaction is provided by air purge gas stream, as is described in preferred embodiments, there is danger of interruptions of air feed to the compressor during periods when the adsorbers (of multiple adsorber systems) are switching from regeneration to adsorption duty, and vice versa. Interrupted flow would be particularly hazardous when the reactor is of the fixed bed type because the reactants are premixed, and interrupted air flow could result in the formation of a flammable gas mixture. Although this problem can be somewhat alleviated by inserting a gas reservoir between the adsorption vessels and the air compressor, this is generally impractical because of the large volume of air fed to the reactor.

The present invention provides a recycle partial oxidation process which avoids the risk of interrupted air feed to the main air compressor, which supplies compressed air to the partial oxidation reactor.

SUMMARY OF THE INVENTION

The present invention is a recycle process for manufacturing a petrochemical by the partial oxidation of a hydrocarbon using air or oxygen-enriched air in the presence of a suitable catalyst under reduced conversion conditions. The reactor effluent contains, inter alia, the petrochemical as the main product, water as a by-product, and unreacted hydrocarbon. The petrochemical is removed from the reactor effluent in a petrochemical recovery unit, and hydrocarbon is adsorbed from the petrochemical unit waste gas using hydrocarbon-selective adsorbents. The invention also includes as steps, purging adsorbed hydrocarbon from the adsorbent with compressed heated air and recycling the hot purged hydrocarbon-air mixture to the partial oxidation reactor, thereby providing part or all of the air requirement of the partial oxidation reaction.

One embodiment of the invention comprises the steps:

(a) contacting in a reaction zone a hydrocarbon with air in the presence of an appropriate oxidation catalyst under conditions which produce a product gas comprising, inter alia, the petrochemical, unreacted hydrocarbon, and moisture;

(b) removing the petrochemical from the product gas in a petrochemical recovery zone, thereby producing a petrochemical-free gas stream containing unreacted hydrocarbon;

(c) subjecting at least part of the petrochemical-free gas remaining after step (b) to a temperature swing adsorption process comprising (1) passing such at least part of the petrochemical-free gas stream through a hydrocarbon-selective adsorbent, thereby adsorbing unreacted hydrocarbon onto the adsorbent and producing a hydrocarbon-depleted waste gas; and (2) at least partially regenerating the hydrocarbon-selective adsorbent by passing compressed, heated purge air therethrough, thereby producing a gaseous stream comprising desorbed hydrocarbon and purge air; and (d) recycling at least part of the gaseous stream comprising desorbed hydrocarbon and air to the reaction zone, thereby providing at least part of the air used in step (a).

In a modification of the above embodiment, step (a) is carried out with oxygen-enriched air by additionally introducing oxygen or oxygen-enriched air into said reaction zone.

Substep (c) (2) of the above embodiment is preferably carried out at a temperature in the range of about 100° to about 250° C.

In a preferred embodiment, the purge air is compressed sufficiently prior to substep (c) (2) to produce the hot gaseous stream at the pressure at which step (a) is carried out.

Preferably, the purge air is heated to the temperature at which it is used in substep (c) (2) solely by heat of compression.

In a preferred embodiment of the invention, step (c) is carried in a plurality of adsorption vessels operated out of phase such that substep (c) (1) is carried in one vessel while substep (c)(2) is carried out in another vessel. In this embodiment the adsorbent in a vessel in which substep (c) (2) is carried out is not cooled substantially prior to its use in substep (c) (1).

Substep (c) (2) is preferably carried out at a pressure in the range of about 2 to about 10 bara. Substep (c) (1) is preferably carried out at a pressure in the range of about 1.2 to about 5 bara. Substep (c)(2) may be carried out at a higher pressure than that at which substep (c) (1) is carried out. In a more preferred embodiment, substeps (c) (1) and (c) (2) are each carried out at a pressure is in the range of about 2 to about 5 bara.

The hydrocarbon-selective adsorbent used in step (c) may be selected from activated alumina, silica gel, activated carbon, faujasite, mordenite, erionite, zeolite 4A, zeolite 5A, zeolite 10X, zeolite 13X and mixtures of these. In such case the petrochemical-free gas and the purge air are preferably dried before passing these gases through the adsorbent.

Alternatively, the hydrocarbon-selective adsorbent may be a hydrophobic adsorbent, particularly a metal cation-free molecular sieve having a silicon-to-aluminum atomic ratio greater than about 100:1 selected from type Y zeolite, type ZSM-5 zeolite, type ZSM-11 zeolite, type ZSM 20 zeolite, silicalite-1, silicalite-2, and mixtures of these. In this case, the relative humidity of one or both of the petrochemical-free gas stream and the purge air are reduced prior to passing them through the bed of adsorbent. The relative humidity of the petrochemical-free gas stream may reduced by heating this stream. Furthermore, the petrochemical-free gas stream may be passed through a water cooler prior to heating this stream to further reduce the moisture content of this stream. The petrochemical-free gas stream may be heated by, for example compressing it.

Step (c) (1) may be carried out with the temperature of the hydrocarbon-selective adsorbent higher than the temperature of the petrochemical-free gas entering the adsorbent.

When the adsorbent is a hydrophobic adsorbent, it is preferably selected from type Y zeolite, type ZSM-5 zeolite, silicalite-1 and mixtures of these.

The method of the invention is particularly suitable for producing maleic anhydride using-butane as the hydrocarbon.

In the above method part of the petrochemical-free gas stream from the petrochemical recovery unit can be recycled directly to said reaction zone. Additionally, part of the air compressed in producing the compressed purge air for step (c) (2) can be sent directly to said reaction zone.

In a preferred embodiment, the gaseous stream comprising desorbed hydrocarbon and purge air is recycled to the reaction zone without further pressurization.

In one aspect of the above-described embodiment, all of the petrochemical-free gas stream is passed through the hydrophobic adsorbent. In another, part of this gas stream is passed through the adsorbent, and the rest is recycled directly to the reaction zone.

In a preferred embodiment, the hydrocarbon adsorbent is a hydrophobic adsorbent which is a metal cation-free molecular sieve having a silicon-to-aluminum atomic ratio greater than about 100:1, and it is selected from type Y zeolite, type ZSM-5 zeolite, type ZSM-11 zeolite, type ZSM-20 zeolite, silicalite-1, silicalite-2, and mixtures of these. In a more preferred embodiment, the adsorbent is selected from type Y zeolite, type ZSM-5 zeolite, silicalite-1 and mixtures of these, and in the most preferred embodiment, the adsorbent is silicalite-1.

In a second embodiment of the invention, a non-hydrophobic hydrocarbon-selective adsorbent is used and both the petrochemical-free gas and the air are dried before passing these gases through the bed of hydrocarbon-selective adsorbent. This is preferably accomplished by subjecting these gases to temperature swing adsorption drying processes in a system comprised of pluralities of beds of moisture-selective adsorbent which are operated out of phase and in such a manner that there is always one or more beds of adsorbent in petrochemical-free gas drying service, always one or more beds of adsorbent in air drying service and always one or more beds of adsorbent being regenerated. The one or more beds of adsorbent undergoing regeneration are preferably at least partially regenerated by passing hydrocarbon-depleted waste gas or dried air through the beds.

Step (c) (1) is generally carried out at a pressure in the range of about 1.2 to 5 bara, and preferably at a pressure in the range of about 1.2 to about 1.75 bara, and step (c) (2) is carried out at a pressure in the range of about 2.0 to about 10 bara, and preferably at a pressure in the range of about 2.0 to about 5 bara.

When a hydrophobic adsorbent is used in the process of the invention, the relative humidity of the petrochemical-free gas stream is preferably reduced prior to passing this gas through the bed of hydrophobic adsorbent. In one aspect of this embodiment, the relative humidity of the petrochemical-free gas stream is reduced by heating this stream, and in another aspect, the petrochemical-free gas stream is passed through a direct contact water cooler prior to heating this stream. This stream can also be heated by compression. As an alternative to heating the petrochemical-free gas, the hydrophobic adsorbent can be heated to a temperature that is higher than the temperature of the petrochemical-free gas.

In other separate or combined preferred embodiments, the hydrocarbon-selective adsorbent is silicalite; the concentration of unreacted hydrocarbon remaining in the product stream produced by the partial oxidation reaction is not greater than about 1% by volume; the partial oxidation product is maleic anhydride; and the hydrocarbon is n-butane.

BRIEF DESCRIPTION OF THE DRAWING

The figure illustrates, in a block diagram, a system in which preferred embodiments of the process of the invention can be carried out.

DETAILED DESCRIPTION OF THE INVENTION

The process of the invention can be applied to any partial oxidation reaction in which a gaseous hydrocarbon is reacted with oxygen, provided in the form of air or oxygen-enriched air, in the presence of an appropriate catalyst to produce a gaseous product stream containing the petrochemical and unreacted hydrocarbon; the petrochemical is separated from the gaseous product stream, leaving a petrochemical-free stream that contains unreacted hydrocarbon; the unreacted hydrocarbon is adsorbed from the remaining gaseous product stream by adsorption; and the adsorbed hydrocarbon is desorbed from the bed of adsorbent and recycled to the partial oxidation reactor. By oxygen-enriched air is meant air that contains more oxygen than is naturally present in air. Typical of such processes are those used to manufacture cyclic anhydrides, such as maleic anhydride, alkylene oxides, such as ethylene oxide, aldehydes, such as acetaldehyde, nitriles, such as acrylonitrile, and chlorinated hydrocarbons, such as vinyl chloride. The details of such partial oxidation reaction-based processes are well known and form no part of the present invention. These processes are described in detail in U.S. Pat. Nos. 5,126,463, 5,262,547, and 5,278,319, the specifications of which are incorporated herein by reference.

The petrochemical manufacturing processes in which the subject invention is employed are those in which some or all of air that is used in the partial oxidation reaction is introduced into the system in the hydrocarbon recovery section of the plant as a purge gas to desorb adsorbed hydrocarbon from the adsorbent. Supplemental air, oxygen-enriched air or oxygen may be supplied directly to the reactor, if desired.

The adsorbent used to adsorb the unreacted hydrocarbon from the petrochemical-free effluent gas from the petrochemical recovery unit may be any adsorbent that selectively adsorbs the unreacted hydrocarbon. The particular hydrocarbon-selective adsorbent used in the process of the invention does not constitute a critical part of the invention. Suitable adsorbents are commercially available and their preparation forms no part of the invention.

In a first embodiment of the invention, the hydrocarbon-selective adsorbent is preferably selected from activated alumina, silica gel, activated carbon, molecular sieves, such as natural zeolites, including faujasite, mordenite, erionite, etc., and synthetic zeolites, including 4A, 5A, 10X, 13X zeolites, etc. Preferred adsorbents for use in this embodiment are silica gel, activated carbon, zeolite 5A and zeolite 13X.

In second embodiment, the hydrocarbon-selective adsorbent is a hydrophobic adsorbent. In this case the adsorbent is substantially metal cation-free and alumina-deficient, i.e. their lattice structures are substantially free of alumina groups. Specifically, they have silicon to aluminum atomic ratios of at least 100.

As this ratio increases the hydrophobicity of the adsorbent improves. Included in this group of adsorbents are molecular sieves of the FAU, MFI and MEL type structures, including zeolites that have been made alumina-deficient by dealumination and molecular sieves that are directly synthesized without introducing alumina groups into the lattice structure. Alumina-deficient molecular sieves useful in the invention include dealuminated type Y zeolite (DAY), ZSM-5, ZSM-11 and ZSM-20, all having silicon to aluminum atomic ratios of at least about 100. Other synthesized molecular sieves that are substantially free of alumina groups which are useful in the invention include those having structures analogous to ZSM-5 and ZSM-11, known as silicalite-1 and silicalite-2, respectively, each of which are substantially free of alumina groups in their structures. Preferred molecular sieves are DAY, alumina-deficient ZSM-5 and silicalite-1, all of which are substantially metal cation-free and all of which are commercially available. For purposes of this invention the term "metal cation-free" means that the adsorbent contains no more than trace amounts of metal cations, and the terms "alumina-deficient" and "dealuminated", when used in reference to molecular sieves mean that the ratio of silicon to aluminum atoms in the sieves is at least about 100:1, i.e., the ratio of silica to alumina groups in the sieve is at least 200:1.

The invention can be better understood from the accompanying drawing. Depicted in the drawing as essential equipment units, are hydrocarbon partial oxidation reactor A, petrochemical product recovery unit B and separator C. Auxiliary equipment, including valves, compressors and heat exchangers, which are unnecessary for an understanding of the invention have been omitted from the drawing to simplify discussion of the invention.

On its inlet end, reactor A is provided with hydrocarbon feed inlet means 2 and hydrocarbon recycle and air supply line 4. Alternatively, the hydrocarbon and oxidant can be premixed and introduced together into reactor A. Reactor A may also be provided additional oxygen through supplemental oxygen or oxygen-enriched air supply line 6, which is shown as being connected to line 4. On its outlet end reactor A is provided with product gas discharge line 8. Reactor A may be any suitable reactor, such as,, for example, those of the fixed, moving, fluidized, or transport catalyst bed design. The invention is particularly suitable for use in systems in which reactor A is a fixed-bed reactor with premixed reactants, because in such reactors the effluent generally does not contain more than about 1% by volume of unreacted hydrocarbon, after removal of petrochemical product. Reactor A may be equipped with heat exchange means (not shown) to remove heat developed in the reaction, which is exothermic. The design details of partial oxidation reactors useful in the process of the invention are well known and form no part of the present invention.

Line 8 is connected to the petrochemical feed inlet of petrochemical product recovery unit B, which may be any unit that functions to separate petrochemical partial oxidation products from byproduct gases. For example, unit B may be a conventional gas scrubber, i.e. an absorber, of, for example, the packed bed design, or it may be a condenser or other appropriate product recovery unit. It is here illustrated as equipped with means for spraying water or an aqueous or nonaqueous liquid on the product gas entering this unit from reactor A. To simplify the description of the process of the invention, recovery unit B will be referred to as a scrubber. Scrubber B receives a scrubbing liquid through inlet 10 and discharges a liquid product through outlet 12. Scrubber B is also equipped with a scrubbed gas outlet 14 which, in the embodiment illustrated in the drawing, is connected to separator C inlet manifold 16.

Separator C may comprise a single adsorption unit or battery of adsorption units operated in phase, or a plurality of adsorption units or batteries of adsorption units operated out of phase, whichever is desired. When a system comprising a single adsorption unit or an "in phase" battery of units is used, the adsorption step must be periodically stopped to permit regeneration of the adsorbent bed(s), whereas when a plurality of adsorption units are employed in parallel and operated out of phase, one or more units can be in adsorption service producing purified adsorbate, while one or more other units are undergoing regeneration to release the adsorbed hydrocarbon. Operation of the hydrocarbon adsorption system is cyclical. A partial cycle (half-cycle, when two beds are used) occurs when one bed has undergone all of the steps in the adsorption process, and a full cycle occurs when each bed of the adsorption system has undergone a partial adsorption cycle. In the complete adsorption process full cycles are repeatedly carried out, so that the process is substantially continuous. In the preferred embodiment of the invention, separator C is a twin bed system comprising a pair of parallel vessels, 18, 20, each packed with one or more hydrocarbon-selective adsorbents of the type described above and operated 180° out of phase, and the invention will be described in detail as practiced in such an arrangement. It is understood, however, that the illustrated system is merely exemplary of systems suitable for practicing the process of the invention.

Feed gas entering feed manifold 16 can be directed to vessel 18 via valve 22 and line 24 or to vessel 20 through valve 26 and line 28. On the outlet end of separator C, nonadsorbed gas passes out of vessel 18 and into nonadsorbed gas outlet manifold 30 through line 32 and valve 34 and out of vessel 20 through line 36 and valve 38. Nonadsorbed gas outlet manifold communicates with nonadsorbed gas discharge line 40. Separator C is also provided on its nonadsorbed gas outlet end with purge air supply line 42, which is provided with air compressor 44. Line 42 is connected to purge gas manifold 46, which communicates with line 32 through valve 48 and with line 36 through valve 50. On the inlet end of separator C, lines 24 and 28 communicate with purged gas manifold 52 through valves 54 and 56, respectively. Manifold 52 communicates with hydrocarbon recycle line 4. Compressed air bypass line 58, fitted with valve 60, connects line 42, downstream of compressor 44, with recycle line 4.

In carrying out the process of the invention, a gaseous hydrocarbon and air introduced into reactor A via feed lines 2 and 4 respectively. Supplemental oxygen or oxygen-enriched air may be introduced into reactor A via line 6, if desired. The feed gases entering reactor A contact the catalyst contained therein and react to form the desired petrochemical product. The product gas stream leaving reactor A contains, in addition to the desired petrochemical, carbon dioxide, carbon monoxide and water as by-products. The product stream generally also contains unreacted hydrocarbon, oxygen and nitrogen, and may contain small amounts of other by-products, impurity gases and nonreactive hydrocarbons, as well. In the embodiment illustrated in the drawing, the product gas stream leaves reactor A via line 8 and enters petrochemical product scrubber B. The purpose of unit B is to remove the petrochemical product from the hydrocarbon reactor effluent gas. In scrubber B the product gases are intimately contacted with a solvent for the petrochemical product, which enters scrubber B through line 10. The solvent, which may be water or an aqueous liquid, or a nonaqueous solvent, dissolves substantially all of the petrochemical product out of the product gas stream. The petrochemical product-containing solution leaves scrubber B via line 12 and is usually further treated to recover the petrochemical product.

The scrubbed gas stream leaves scrubber B through line 14, and part or all of this stream is next treated to recover unreacted hydrocarbon from the stream. This is accomplished by passing the scrubbed gas through separator C, which contains a hydrocarbon-selective adsorbent of the types described above. Preferred adsorbents are the hydrophobic adsorbents mentioned above, because their use provides two important benefits. Firstly, it makes possible the efficient removal of hydrocarbons from the moisture-laden scrubbed gas stream without first removing moisture from this stream. Secondly, it permits purging of adsorbed hydrocarbon from the adsorbent using ambient air (which contains moisture) as a purge gas without danger of loading the adsorbent with water. When hydrophobic adsorbents are used the moist air leaving the adsorption units in the purge gas stream can be used to provide part or all of the oxygen requirement for the partial oxidation reaction, since the use of moist air as a source of oxygen is usually not detrimental to the partial oxidation reaction taking place in reactor A.

When using a hydrophobic adsorbent as the hydrocarbon-selective adsorbent it is usually desirable to reduce the relative humidity of the gases passing through the adsorbent. Although some hydrophobic adsorbents can function with fully moisture-saturated gases without suffering adverse effects, it is usually preferred that the gas be somewhat less than 100% saturated with moisture. This reduces the risk of condensation of moisture onto the adsorbent, which would damage the adsorbent. It is often desirable to reduce the relative humidity of the scrubbed gas to about 90% or lower, and most preferred to reduce it to about 80% or lower.

Reduction of the relative humidity of the scrubbed gas can be accomplished in a number of ways. It can be cooled sufficiently to cause some of the moisture in the stream to condense, and then heated, thus causing the relative humidity to drop. Alternatively, it may be preferable to simply heat the gas without first cooling it to the point of supersaturation. Heating the gas increases its moisture capacity, thereby reducing its relative humidity. Heating of the petrochemical recovery effluent gas stream can be accomplished by compressing it. This procedure is convenient when it is desired to raise the pressure of the gas stream prior to introducing it into separator C. Reduction of the relative humidity of the petrochemical recovery gaseous effluent is described in detail in the above-mentioned U.S. patent application Ser. No. 457,003, and this step forms no part of this invention.

When adsorbents other than nonhydrophobic adsorbents are used in the process of the invention, it is desirable to remove water from the scrubbed hydrocarbon-containing gas stream prior to passing it into separator C; otherwise the capacity of the adsorbent will be severely reduced by the preferential adsorption of water vapor. Similarly, it is usually desirable to remove water vapor from the purge air prior to its introduction into separator C so that it will be more effective in removing moisture from the adsorbent during the regeneration step.

As the petrochemical-free effluent from unit B passes through separator C it is only necessary to remove sufficient byproduct gases (carbon oxides and moisture) and inert gases (nitrogen and argon) to prevent the buildup of these gases in the system. This is accomplished when the quantity of carbon oxides and moisture removed from the system is equivalent to the amount of byproduct generated in reactor B, and when the quantity of inert gases removed is equivalent to the quantity of inert gases introduced into the system in each pass. Thus, it is usually desirable to send to separator C only the volume of scrubbed gas that is necessary to maintain the proper material balance. The remainder of the scrubbed gas stream can be recycled directly to reactor A through a direct recycle line (not shown).

The process of the invention is practiced as a cyclical TSA process. The hydrocarbon adsorption step can be economically carried out at pressures up to about 10 bara (bar, absolute) or higher; however, it is usually carried out at pressures not in excess of about 5 bara, for example at pressures in the range of about 1.2 to about 5 bara. In general, it is preferred to conduct the hydrocarbon adsorption step at pressures that render this step most congruous with other steps of the overall process. The scrubbed gas from scrubber B is generally available at pressures up to about 2 bara. Operating the hydrocarbon adsorption process at adsorption pressures in the range of about 1.2 to about 1.75 bara will enable the scrubbed gas stream to pass through the hydrocarbon adsorbers and to reach a downstream incinerator (or other disposal means) without the use of supplemental blowers or compressors. Accordingly, it is preferred to conduct the adsorption step at pressures in the range of about 1.2 to about 1.75 bara.

The temperature at which the hydrocarbon adsorption step is carried out is not critical. In general, the adsorption is carried out at temperatures in the range of about 5° C. to about 50° C., and it is most often carried out at temperatures in the range of about 20° to about 40° C. The adsorption is preferably carried out at the temperature which provides optimum separation and which is in harmony with other steps of the product manufacturing process, if possible. The optimum adsorption temperature of the process will depend, inter alia, upon the particular adsorbent being used, the temperature and relative humidity of the gas being separated, the pressure at which the process is carried out, the specific gases being separated, etc. Those skilled in the art can determine which operating conditions are best suited for their purposes.

A key feature of the hydrocarbon adsorption process is the step of purging the adsorption beds with air. This step serves the dual purpose of purging hydrocarbon from the beds and providing some or all of the oxygen required for the partial oxidation reaction. The bed regeneration step is carried out at a temperature higher than the temperature at which the hydrocarbon adsorption step is carried out. In general, adsorbent regeneration is carried out at a temperature in the range of about 100° to about 250° C., and it is preferably carried out at a temperature in the range of about 125° to about 200° C. Although supplemental heating of the purge gas or the adsorbent can be provided, the step of compressing the purge gas to the desired pressure is generally sufficient to raise its temperature to the desired adsorbent regeneration temperature.

Compressor 44 is the main feed air compressor for reactor A. An important feature of the invention is the placement of hydrocarbon adsorption separator C downstream of compressor 44. By arranging the system in this manner it is unnecessary to provide a supplemental air blower to provide purge gas to separator C at superatmospheric pressure. Additionally, compressing the purge gas to a pressure sufficiently high to use the purge gas in reactor A without additional compression provides the additional advantage of heating the purge gas to the temperature at which it is desirably used to regenerate the adsorbent in vessels 18 and 20.

Compressor 44 is generally designed to raise the pressure of the purge gas to about 2 to about 10 bara, or higher. In preferred embodiments of the invention, the purge gas entering separator C is at a pressure in the range of about 2 to about 5 bara. It can be appreciated that the pressure of the purge gas passing through separator C during bed regeneration may be higher than the pressure of the hydrocarbon-containing gas passing through separator C during the adsorption step.

The operation of separator C will be described first with the bed in vessel 18 in the adsorption mode and the bed in vessel 20 in the regeneration mode, and then the bed in vessel 20 in the adsorption mode and the bed in vessel 18 in the regeneration mode. In the first half of the cycle, valves 22, 34, 50 and 56 are open and all other valves associated with separator C are closed. The scrubbed feed gas passes through line 24 and enters vessel 18. If the hydrocarbon-selective adsorbent is not a hydrophobic adsorbent, it is desirable to dry the gas before it enters the adsorbent. This can be accomplished by passing the gas through a desiccant positioned upstream of vessels 18 and 20. The gas drying step is preferably operated on a TSA cycle. When the desiccant becomes saturated with water it can be regenerated by passing through it a heated dry gas, such as part of the gas passing out of separator C through line 40. If the hydrocarbon-selective adsorbent is a hydrophobic adsorbent it is not necessary to dry the gas, put it is preferred to reduce its relative humidity. This can be accomplished in the manner described above.

As the gas passes through the adsorbent in vessel 18, unreacted hydrocarbon is preferentially adsorbed therefrom.

The gas stream leaving vessel 18, now depleted in hydrocarbon, passes through line 32 and leaves the adsorption system through manifold 30 and line 40.

During the bed regeneration step(s), air, pressurized and heated to the desired pressure and temperature by compressor 44 is introduced into the vessel 20 through line 42, manifold 46 and line 36. If the hydrocarbon-selective adsorbent is not a hydrophobic adsorbent it is desirable to dry the air prior to its passage through the adsorbent. This can be accomplished by passing the air through a desiccant. The desiccant can be regenerated by passing through it a hot gas, such as the hot compressed air exiting compressor 44. The compressed, hot purge air passes through the adsorption bed in vessel 20, thereby desorbing hydrocarbon from the bed and sweeping the desorbed hydrocarbon from the vessel. The desorbed hydrocarbon and purge gas leave vessel 20 through line 28 and manifold 52, and are conveyed to reactor A through line 4.

As the adsorption step proceeds, the unreacted hydrocarbon adsorbed gas front progresses through the bed in vessel 18 toward the outlet end of this vessel. When the adsorbed hydrocarbon front reaches a predetermined point in vessel 18, the first half of the cycle is terminated and the second half is begun.

During the second half of the adsorption cycle, the bed in vessel 20 is put into adsorption service and the bed in vessel 18 is regenerated. During this half-cycle valves 26, 38, 48 and 54 are open and all other valves associated with separator C are closed. Unreacted hydrocarbon gas now enters vessel 20 through line 28, passes through the bed of adsorbent in this vessel, and exits separator C through line 36, manifold 30 and line 40. Meanwhile the bed in vessel 18 is being regenerated. During regeneration of the bed in vessel 18, the purge gas passes into vessel 18 via line 42, manifold 46 and line 32, and desorbed hydrocarbon and purge gas exit this vessel through line 24 and manifold 52, and are conveyed to reactor A through line 4. When the hydrocarbon adsorption front reaches a predetermined point in the bed in vessel 20, the second half of the cycle is terminated and the full cycle is repeated.

The process of the invention is particularly suitable for systems in which the petrochemical-depleted gas passing through line 14 contains not more than about 1% by volume of hydrocarbon. In such situations it is not necessary to cool a bed of adsorbent which has just finished its regeneration step prior to its being put into hydrocarbon adsorption service. It has been determined that when the hydrocarbon-containing gas contains not more than 1% by volume hydrocarbon, the adsorbent will cool quickly enough as the hydrocarbon-containing gas passes through it to adsorb all of the hydrocarbon before any hydrocarbon passes out of the nonadsorbed outlet of the vessel in adsorption service. Preferably the hydrocarbon content of the feed gas to separator C will not exceed about 0.5% by volume, and most preferably it will not exceed about 0.4% by volume. The process of the invention is particularly suitable for use with fixed-bed reactor systems, since the hydrocarbon concentration of the effluent from the petrochemical recovery unit of these systems generally falls within the above ranges.

It will be appreciated that it is within the scope of the present invention to utilize conventional equipment to monitor and automatically regulate the flow of gases within the system so that it can be fully automated to run continuously in an efficient manner.

The invention is further illustrated by the following hypothetical example in which percentages, ratios, and parts, including parts per million (ppm), are on a volume basis, unless otherwise indicated.

EXAMPLE

This example is designed to be carried out in a 20,000 metric ton per year maleic anhydride production plant which forms part of a system like that illustrated in the appended drawing. The maleic anhydride is produced in a partial oxidation process by the reaction of oxygen (provided as air) and butane using a fixed bed catalyst. The adsorbent beds in the adsorption vessels have an internal diameter of 3.9 meters (m), a bed height of 0.84 m and a total capacity of 10 $m^3$. The adsorbent used in the vessels is silicalite-1. The adsorption process is designed to operate on a four hour cycle in which an adsorption stage of 240 minutes is carried out in one of the two vessels while a regeneration stage comprising a 30 min. pressurization step, a 200 min. bed regeneration step and a 10 min. depressurization step. The air compressor which supplies bed regeneration air produces 910 kilogram-moles per hour (kgmols/hr) of air at a pressure of 3.1 bara and a temperature of 130° C. Of this air stream, 200 kgmols/hr is used for bed regeneration and the other 710 kgmols/hr bypasses the adsorption system and is sent directly to the partial oxidation reactor as feed air. The bed regeneration air is heated in an auxiliary heater to a temperature of 250° C. prior to its introduction into the bed being regenerated.

At the startup of the bed regeneration stage of the process the bed being regenerated will be pressurized to a pressure of 3.1 bara by incoming air. When the adsorption vessel pressure reaches this pressure the bed regeneration outlet valve is opened and the purge air, together with desorbed butane will be transported to the air feed line where it is combined with the bypass air from the air compressor. This gas mixture is introduced into the partial oxidation reactor as part or all of the air supply to the reactor. Upon completion of the bed regeneration step the pressure in the adsorption vessel will be reduced to ambient pressure by discharge of the air in the adsorption vessel to the air feed line to the partial oxidation reactor or to the environment. This will complete the bed regeneration stage of the process.

Upon completion of bed regeneration the temperature in the regenerated adsorbent will be about 100° to about 130° C. Waste gas from the maleic anhydride recovery unit containing about 0.3% n-butane and at a temperature of 50° C. is fed directly into the hot adsorber. The waste gas feed will rapidly cool the adsorption vessel to about 50° C. without breakthrough of butane from the adsorption vessel. The adsorption step then continues for the full duration of the adsorption stage.

The above example illustrates an embodiment of the process of the invention wherein the pressure during the bed regeneration step is higher than the pressure during the adsorption step of the butane recovery process. As indicated, the process provides an uninterrupted flow of pressurized air to the partial oxidation reactor, and waste gas feed to the freshly regenerated adsorbent can begin without cooling the adsorbent in the adsorption vessel.

Although the invention has been described with particular reference to a specific equipment configuration and to specific steps these are merely exemplary of the invention, and variations are contemplated. The scope of the invention is limited only by the breadth of the appended claims.

What is claimed is:

1. A method of producing a petrochemical comprising the steps:

(a) contacting in a reaction zone a hydrocarbon with air in the presence of an appropriate oxidation catalyst under conditions which produce a product gas containing said petrochemical, unreacted hydrocarbon and moisture;

(b) removing said petrochemical from said product gas in a petrochemical recovery zone, thereby producing a petrochemical-free gas stream containing unreacted hydrocarbon;

(c) subjecting at least part of said petrochemical-free gas stream to a temperature swing adsorption process comprising (1) passing said at least part of said petrochemical-free gas stream through a hydrocarbon-selective adsorbent, thereby adsorbing unreacted hydrocarbon onto said adsorbent and producing a hydrocarbon-depleted waste gas;

(2) at least partially regenerating said hydrocarbon-selective adsorbent by passing therethrough air that has been compressed and thereby at least partially heated to the desired regeneration temperature, thereby producing a gaseous stream comprising desorbed hydrocarbon and purge air; and (d) recycling at least part of said gaseous stream to said reaction zone, thereby providing at least part of the air used in step (a).

2. The method of claim 1, comprising carrying out step (a) with oxygen-enriched air by additionally introducing oxygen or oxygen-enriched air into said reaction zone.

3. The method of claim 1, wherein substep (c) (2) is carried out at a temperature in the range of about 100° to about 250° C.

4. The method of claim 3, wherein said purge air is compressed sufficiently prior to substep (c) (2) to produce said gaseous stream at the pressure at which step (a) is carried out.

5. The method of claim 3, wherein said purge air is heated to the temperature at which it is used in substep (c) (2) solely by heat of compression.

6. The method of claim 3, wherein step (c) is carried in a plurality of adsorption vessels operated out of phase such that substep (c) (1) is carried out in one vessel while substep (c)(2) is carried out in another vessel.

7. The method of claim 6, wherein the adsorbent in a vessel in which substep (c) (2) is carried out is not cooled substantially prior to its use in substep (c) (1).

8. The method of claim 1 or claim 4, wherein substep (c) (2) is carried out at a pressure in the range of about 2 to about 10 bara.

9. The method of claim 8, wherein substep (c) (1) is carried out at a pressure in the range of about 1.2 to about 5 bara.

10. The method of claim 8, wherein substep (c)(2) is carried out at a higher pressure than that at which substep (c) (1) is carried out.

11. The method of claim 1 or claim 4, wherein substeps (c) (1) and c) (2) are each carried out at a pressure is in the range of about 2 to about 5 bara.

12. The method of claim 1, wherein said hydrocarbon-selective adsorbent is selected from activated alumina, silica gel, activated carbon, faujasite, mordenite, erionite, zeolite 4A, zeolite 5A, zeolite 10X, zeolite 13X and mixtures of these.

13. The method of claim 12, wherein said petrochemical-free gas and said purge air are dried before passing these gases through said adsorbent.

14. The method of claim 13, wherein said petrochemical-free gas and said purge air are dried by passing them through a desiccant selected from silica gel, alumina and zeolite 3A.

15. The method of claim 14, wherein said desiccant is regenerated by purging it with the hydrocarbon-free waste gas produced in step (c) (1).

16. The method of claim 1, wherein said hydrocarbon-selective adsorbent is a metal cation-free molecular sieve having a silicon-to-aluminum atomic ratio greater than about 100:1 selected from type Y zeolite, type ZSM-5 zeolite, type ZSM-11 zeolite, type ZSM 20 zeolite, silicalite-1, silicalite-2, and mixtures of these.

17. The method of claim 16, further comprising reducing the relative humidity of one or both of said petrochemical-free gas stream and said purge air prior to passing them through said bed of adsorbent.

18. The method of claim 17, wherein the relative humidity of said petrochemical-free gas stream is reduced by heating this stream.

19. The method of claim 18, further comprising passing said petrochemical-free gas stream through a water cooler prior to heating this stream.

20. The method of claim 18, wherein said petrochemical-free gas stream is heated by compression.

21. The method of claim 17, wherein during substep (c) (1) the temperature of said hydrocarbon-selective adsorbent is higher than the temperature of said petrochemical-free gas.

22. The method of claim 16, wherein said adsorbent is selected from type Y zeolite, type ZSM-5 zeolite, silicalite-1 and mixtures of these.

23. The method of claim 1, wherein said cyclic anhydride is maleic anhydride and said hydrocarbon is n-butane.

24. The method of claim 1, wherein part of said petrochemical-free gas stream is recycled directly to said reaction zone.

25. The method of claim 1, wherein part of the air compressed in producing said compressed purge air for step (c) (2) is transported directly to said reaction zone.

26. The method of claim 1, wherein the petrochemical-free gas stream produced in step (b) contains not more than about 1% by volume unreacted hydrocarbon.

* * * * *